United States Patent [19]

Cornelius

[11] Patent Number: 4,905,701

[45] Date of Patent: Mar. 6, 1990

[54] APPARATUS AND METHOD FOR DETECTING SMALL CHANGES IN ATTACHED MASS OF PIEZOELECTRIC DEVICES USED AS SENSORS

[75] Inventor: George Cornelius, Milford, Mass.

[73] Assignee: National Research Development Corporation, London, England

[21] Appl. No.: 206,768

[22] Filed: Jun. 15, 1988

[51] Int. Cl.$^4$ .............................................. A61B 8/00
[52] U.S. Cl. ........................... 128/660.01; 422/68.1; 73/53; 436/806
[58] Field of Search ............... 73/19, 24, 32 A, 53–54, 73/59; 128/631, 738, 632, 660.01; 374/117; 310/313 R, 313 B; 333/150–152; 324/71.1; 436/806; 422/68

[56] References Cited

U.S. PATENT DOCUMENTS

| | | | |
|---|---|---|---|
| 4,314,821 | 2/1982 | Rice | 436/806 X |
| 4,361,026 | 11/1982 | Muller et al. | 73/23 |
| 4,398,115 | 8/1983 | Gagnepain et al. | 374/117 |
| 4,691,714 | 9/1987 | Wong et al. | 128/738 |
| 4,735,906 | 4/1988 | Bastiaans | 436/527 |

OTHER PUBLICATIONS

"Palladium–Surface Acoustic Wave Interaction for Hydrogen Detection", by A. d'Amico, Appl. Phys. Lett. 41 (3), 1st Aug. 1982.

"Piezoelectric Crystals as Detectors in Liquid Chromatography", by P. L. Konash and G. J. Bastiaans, Anal. Chem., 1980, 52, pp. 1929–1931.

"Liquid–Phase Piezoelectric and Acoustic Transmission Studies on Interfacial Immuno Chemistry", by M. Thompson, C. L. Arthur and G. K. Dhaliwal, Anal. Chem., 1986, 58, pp. 1206–1209.

"Surface Acoustic Wave Probe for Analysis. I. Introduction and Instrument Description", by H. Wohltjen and R. Dessy, Analytical Chemistry, vol. 51, No. 9. Aug. 1979, pp. 1458–1464.

*Primary Examiner*—Francis Jaworski
*Attorney, Agent, or Firm*—Cushman, Darby & Cushman

[57] ABSTRACT

In analysis, particularly for medical diagnostics, material can be selectively bound to the surface of a piezoelectric crystal by a reagent. The amount of material so bound affects the speed of propagation of an acoustic wave launched and received on the crystal surface by respective electrode pairs. Previously the crystal was used as a resonant element in an oscillator controlling the frequency of oscillation and so indicating the amount of bound material. However, the oscillator was either unstable or the range of bound masses too small to be of practical use. In the present invention delay between launch and reception of the acoustic wave provides a control signal for a voltage controlled oscillator. A much more stable system can therefore be constructed with a wide working range and high stability since the crystal is no longer the resonant element. Much greater sensitivity is also possible since the oscillator frequency may be greatly increased. A control signal representative of delay may be produced by a phase comparator comparing the phase of two input signals: one direct from the oscillator, and one from the reception of an acoustic wave on the crystal surface launched using a signal from the oscillator. The signal to the crystal may be modulated using a low frequency oscillator before it reaches the crystal to aid the oscillator in following frequency changes due to changing crystal surface conditions and the resulting signal may be summed with the output of a resonance oscillator before application to the crystal to aid the oscillator in initially settling to a stable frequency.

19 Claims, 2 Drawing Sheets

APPARATUS AND METHOD FOR DETECTING SMALL CHANGES IN ATTACHED MASS OF PIEZOELECTRIC DEVICES USED AS SENSORS

BACKGROUND OF THE INVENTION

The present invention relates to detecting changes which affect the speed of propagation of acoustic waves in crystals, and particularly to piezoelectric crystals used as chemical and/or medical diagnostic sensors, when used in the surface acoustic wave (SAW) mode in which a selective coating is applied to a crystal and a sample which is to be analysed is placed in contact with the crystal. Should an analyte be present (that is an entity whose presence is to be detected) then the mass attached to the crystal changes and the natural frequency of oscillation of the crystal varies.

The first piezoelectric mass detection was reported by King (Anal. Chem. 1964, 36, 1735) and relies on using selective deposition of mass to perturb the shear-thickness mode of oscillation of a quartz plate sandwiched between two thin metal electrodes. The condition of resonance for this configuration occurs when the voltage across the electrodes is applied at a frequency, f, equal to the ratio of the wave velocity in the material to twice the thickness. Mass detection is achieved by monitoring frequency changes upon exposure of a coated oscillating crystal to the vapor of interest. This mode of operation is known as the bulk acoustic wave (BAW) mode.

At the moment about twelve quartz BAW devices are commercially available for monitoring gaseous compounds such as sulfur dioxide, ammonia, hydrogen sulfide and pesticides in air. These devices rely on carefully chosen coatings to bind the analyte of interest to the crystal. There appears to be a practical limit to the sensitivity of such devices since frequencies higher than 15 MHz are difficult to handle.

It has also proved possible after initial doubts to employ direct liquid-phase detection for crystals operating in the BAW mode in spite of the large acoustic dampening effect of a drop of liquid such as water on the crystal. Liquid-phase detection has paved the way for the detection of more interesting analytes such as proteins which can be selectively deposited on to crystal surfaces by first activating the surfaces with antibodies to the particular analyte to be determined. Indeed, the use of antibodies (as in many well known commercial immunoassays) enables detection of a very broad spectrum of analytes from drugs to viruses. The practical limit on operating frequency and therefore sensitivity for liquid phase is similar to that for gas phase mentioned above. For this reason attention has been turned to surface acoustic wave (SAW) devices since the practical limit on operating frequency is much higher. In addition, SAW devices are much more readily integrated into microelectronic structures and allow more compact devices and instrumentation.

In surface acoustic waves particles near the crystal surface have displacements with two components: a longitudinal component (back and forth, parallel to the surface) and a shear vertical component (up and down). The energy of these surface waves is localised within one or two acoustic wavelengths of the surface allowing strong interaction of the acoustical energy with the medium adjacent to the surface. For chemical sensing, the adjacent medium is a selective coating and mass loading of the device by absorption into this coating is used to perturb the surface acoustic wave and provide a signal.

A typical SAW device comprises two sets of interdigital transducer electrodes usually 0.1 to 0.2 microns thick which are vacuum deposited on to a polished piezoelectric substrate. A radio frequency voltage is applied between the fingers of one set of electrodes thereby launching a wave which is picked up by the other electrode set after propagation through the coating. By feeding the output of the second set of electrodes back through an amplifier to the first set of electrodes the SAW device becomes a resonating element of an oscillator circuit. The frequency of the propagating wave depends on the surface wave velocity in the particular substrate used and the center to center spacing of the two sets of electrodes. If an adsorbing analyte perturbs the mass of the selective coating then the resulting mass loading results in a reduction in wave velocity and a corresponding change in resonant frequency.

Some early prototype uses of SAW devices for liquid-phase mass detection have been carried out but they suffer from three disadvantages. Firstly the loading ranges which can be used and still obtain stable oscillation are very small, secondly the oscillations are unstable with temperature variation, and thirdly noise levels are high masking variations in output frequency.

As to the first of these disadvantages, the oscillator circuit using the SAW device as a resonating element only generates a stable frequency if shifts in frequency due to surface conditions on the crystal are small. Thus if a load of 20 microliters of water is added to the surface, a change in frequency of only 10 KHz occurs which indicates that the system is not sensitive enough to detect the small changes in mass which occur, for example, in medical diagnostics. Usually if liquid is placed on the SAW device the device becomes over damped and oscillation ceases, but if the gain of the amplifier is increased to force oscillation over a wide range of operating conditions then instability results rendering the device useless.

SUMMARY OF THE INVENTION

The present invention provides an improvement in sensitivity and stability for analysis based on acoustic waves across piezoelectric devices (such as piezoelectric crystals or ceramics) by controlling the frequency of an oscillator circuit which does not include a SAW device as a resonant element. Instead the interval between the launch and reception of an acoustic wave on a piezoelectric device is used to derive a control signal controlling the frequency of the oscillator. As the load on the surface of the said device changes, the interval between launching and reception of acoustic waves also changes causing a variation in the oscillator frequency. Since the SAW device is no longer the resonant element of the oscillator, a large change in the loading of the surface of the crystal can be tolerated without destabilishing the output frequency of the oscillator. In addition the oscillator can be operated at, for example, a frequency one to two orders of magnitude higher, thus increasing the sensitivity of the device to changes in mass bound to the surface of the device also by two to four orders of magnitude. Changes in the frequency of oscillation indicate changes in the mass bound to the surface of the device but an alternative indication (which is probably not so accurate) can be obtained from the value of the control signal.

Preferably the interval between the launching and reception of an acoustic wave is monitored by a phase comparator which receives two inputs from the oscillator, one direct and another by way of the SAW device; the output of the phase detector is then representative of the said interval. If a phase comparator is used the oscillator can be regarded as operating in a phase locked loop.

An important advantage of the invention can now be seen: in prior art systems where the piezoelectric device is the resonating element, the amplitude of oscillation is important to stability and varies with surface loading, but in the invention where phase comparison is important amplitude and therefore surface load is largely irrelevant.

The simple arrangement mentioned above suffers from the disadvantage that lock to a stable output frequency does not always occur, and even when lock is established it may be lost again as the oscillator frequency changes due to variations in crystal surface conditions. The latter problem can be overcome to some extent by combining (by summing or modulating) the signal to the SAW device with a low frequency compared with that of the oscillator (for example at least an order of magnitude below). The effect is to provide a noise-like signal on the output of the phase comparator which, when lock is lost, causes the oscillator to sweep until it takes up a frequency at which the output of the phase comparator has the control signal corresponding to that frequency.

On start-up, or if lock is completely lost, then establishing lock is difficult, but, as is explained below, this difficulty can be overcome by using the low frequency to modulate a reference frequency, in the frequency range of the oscillator, before the modulated signal is summed with the oscillator output and applied to launch the acoustic wave on the SAW device.

Usually the surface of the SAW device is prepared by coating it with a reagent, this reagent being sensitive to an analyte in that the reagent tends to bind the analyte to the surface of the device. Thus the invention finds use in medical diagnostic applications where, for example, antibodies can be chemically bound to the surface of the SAW device. When the analyte either contacts the surface of the device in vapour phase or in liquid phase, as a drop of liquid placed on the surface, the antibodies bind the analyte to the surface. Antibodies may be bound to a wide variety of surfaces (see "Immobilised Enzymes, Antigens, Antibodies and Peptides", edited by H. H. Weetall, Dekker, NY, 1975, page 191) and the use of quartz SAW devices presents no special problems since the surface is chemically similar to glass. Thus in practice the liquid or vapour phase containing analyte would be placed in contact with the SAW surface and the resulting change in frequency of the oscillator, in a predetermined interval, gives an indication of the amount of analyte which binds to the surface. A detection limit of the order of 100 picograms is expected to be achieved and provide a much more simple method for low concentration measurements than is available at present using immunoassay techniques requiring several washing and/or reagent exposure steps which are either accomplished manually or by complex instrumentation. The present invention offers the distinct advantage that it can provide a direct indication of specific surface binding as it occurs with excellent sensitivity, thus eliminating the need for conventional enzyme amplification/read-out steps, or any of the other commonly used labelling systems.

Other applications of the invention are also expected in situations where materials become bound to the surface of the SAW device or the speed of propagation of acoustic waves in the device is affected in other ways.

BRIEF DESCRIPTION OF THE DRAWINGS

The invention will now be described, by way of example, with reference to the accompanying drawings, in which.

DESCRIPTION OF THE PREFERRED EMBODIMENT

Figure 1A:
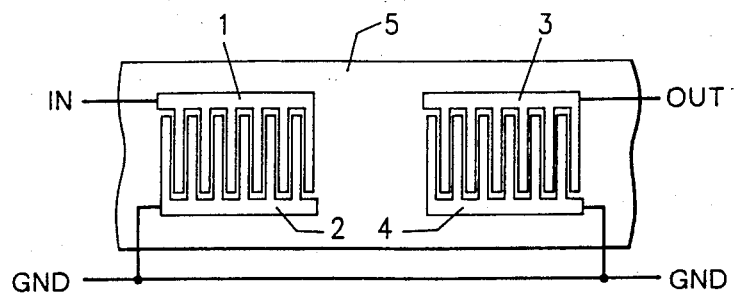
FIGS. 1(a) and 1(b) show electrode arrangements used in some embodiments of the invention.
Figure 1B:
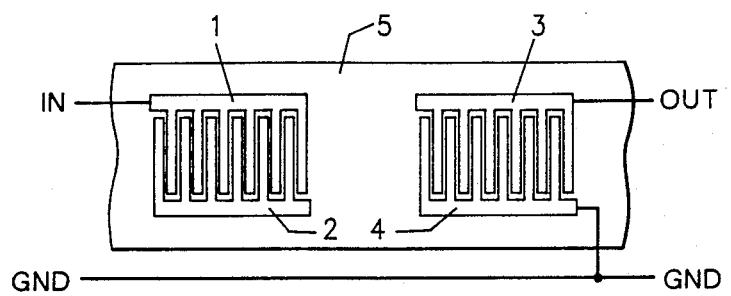

In order to carry out an analysis a piezoelectric crystal coated with a reagent is placed in a holder in which electrode pairs deposited on the crystal surface are connected to a circuit. The electrodes of each pair are interdigitated as shown in FIGS. 1(a) and 1(b), where one electrode pair consists of electrodes 1 and 2 and the other pair consists of electrodes 3 and 4, and the piezoelectric crystal is indicated by the outline 5. One pair of electrodes is used as a transmitter which launches the surface acoustic wave on to the piezoelectric crystal and the other pair is used as a receiver.

Figure 2:
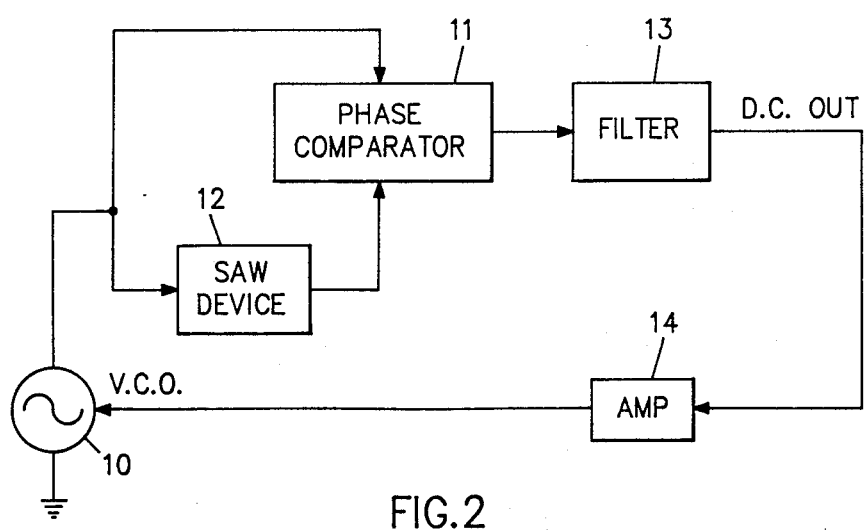
FIG. 2 is a block diagram of a circuit of a simple form of the invention.

In FIG. 2 a voltage controlled oscillator (V.C.O.) 10 is connected to two inputs of phase comparator 11 (commercially known as a phase detector), one of the connections being by way of a surface acoustic wave device (SAW) 12; that is a piezoelectric crystal carrying two spaced apart pairs of interdigitated electrodes which are in close proximity with one another.

The launch electrodes of the phase comparator may be connected in the conventional way as indicated in FIG. 1(a) with the electrode 1 connected to one input terminal, and the electrode 2 connected to a common or ground terminal. Alternatively the launch electrodes may be connected as shown in FIG. 1(b) with the electrode 1 floating and the electrode 2 connected to the "live" (that is non-ground) input terminal of the oscillator 10. A ground terminal of the oscillator 10 and the phase comparator 12 is connected to the electrode 4 but not to either of the launch electrodes 1 and 2. The connections of FIG. 1(b) have some advantage in allowing a surface acoustic wave to propagate over a wider range of mass loadings applied to the crystal surface. A possible explanation for this improved performance is that the residual ground path to the electrode 1 is largely through the applied mass, at least when it is in the form of a drop of liquid. As the surface mass changes the impedance of this ground path also changes and compensates for the change in mass. Thus self compensation is obtained because the surface mass is part of the driving impedance.

In general the two inputs received by the phase comparator 11 are out of phase due to the comparatively slow propagation through the SAW 12 and this phase difference rises with increase in frequency. As a result of the phase difference a d.c. signal is produced at the output of the phase comparator 11 and passed through a noise reduction filter 13 and an amplifier 14 to that terminal of the V.C.O. 10 which controls the frequency of oscillation.

Theoretically the circuit of FIG. 2 stabilises at a frequency such that the delay in the SAW 12 provides a d.c. output from the phase comparator 11 at the output of the amplifier 14 which causes the V.C.O. 10 to generate the frequency which has the previously mentioned delay in the SAW 12. If the surface properties of the SAW 12 change, as occurs when an analyte becomes progressively bound to the surface by a suitable reagent, then the delay in the SAW 12 changes and the loop stabilises at a lower frequency. As a result the change in frequency of the V.C.O. 10 provides an indication of the weight of analyte which has become bound to the surface of the SAW. In practice, the circuit of FIG. 2 has serious disadvantages, mainly that the V.C.O. is often not able to lock on to a fixed frequency and the d.c. amplifier 14 is noisy and causes instability at any fixed frequency which is established. In a modified version the input to the V.C.O. 10 is phase modulated so that the d.c. amplifier 14 can be replaced by an a.c. amplifier but the circuit is still sometimes unable to lock to a stable frequency.

Figure 3:
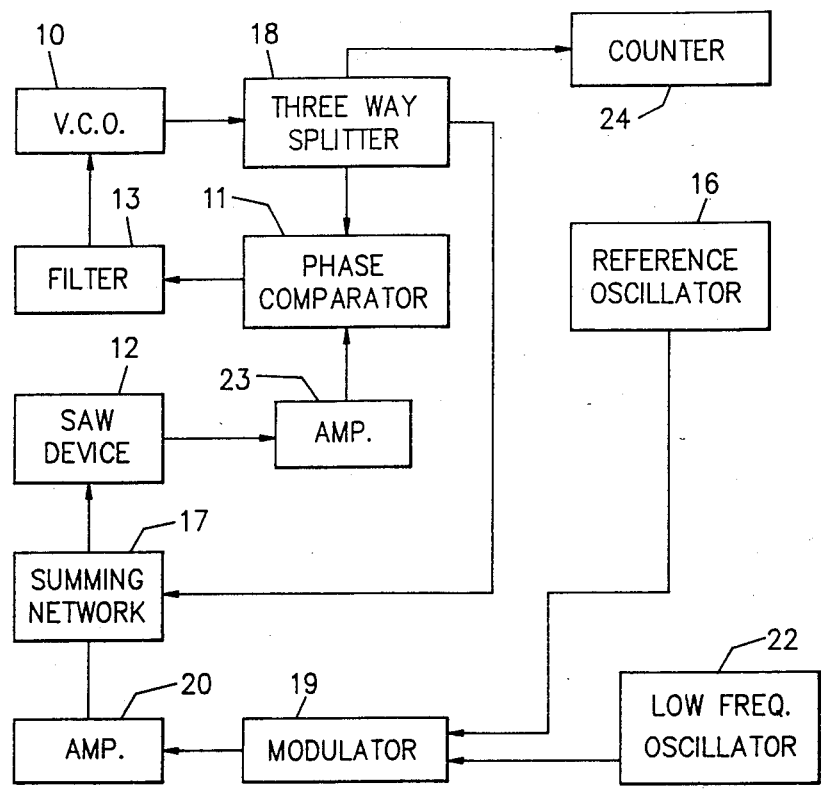
FIG. 3 is a block diagram of a form of the invention using both a modulating oscillator and a reference oscillator.

A circuit which overcomes these problems is shown in FIG. 3 where a pulse modulated signal from a modulator 19 is applied by way of an amplifier 20 and a summing network 17 to the, or one of the, transmit electrodes of the SAW 12. The summing network also receives the output of the V.C.O. 10 after it has passed through a three-way splitter circuit 18. In the modulator 19 a signal from a stable oscillator 16 having a stable reference frequency of about 30 MHz is 100% pulse modulated by the output from a low-frequency rectangular-wave modulating oscillator 22 typically operating at 800 KHz or 400 KHz. The resulting output signal from the modulator 19 is spaced-apart bursts of constant amplitude 30 MHz oscillations, the bursts occurring at a repetition frequency of the modulating oscillating 22. Since a great deal of attenuation occurs in the SAW device 12, an amplifier 23 is connected between the device and one input to the phase comparator 11. The three-way splitter circuit has one output connected to a counter 24 which provides an indication of the frequency of the V.C.O. 10 and therefore also an indication of changes in the amount of analyte bound to the surface of the SAW device. The V.C.O. 10, the SAW device 12, the phase comparator 11 and the filter 13 can be regarded as a phase-locked loop.

Operation is believed to be as follows. At the moment the circuit of FIG. 3 is switched on the output of the V.C.O. 10 can be regarded as drifting in a random way over a wide range of frequencies but the reference oscillator 16 produces a stable frequency output which reaches the phase comparator by way of the circuits 19, 20, 17, 12 and 23 where it is compared with the range of frequencies generated by the V.C.O. 10 and appearing at the other input of the phase comparator 11 by way of the three-way splitter 18. Only that frequency from the V.C.O. 10 which equals the output of the reference oscillator 16 generates an output from the phase comparator 11, the output being dependent on the difference in phase between the two applied signals. Thus a d.c. control signal appears at the output of the phase comparator 11 and is applied through the filter 13 to control the frequency of operation of the V.C.O. 10. As a result the output frequency of the V.C.O. 10 begins to stabilise at the frequency of the reference oscillator 16 (but not necessarily at the same phase due to the phase differences in the various paths to the phase comparator 11). As soon as the V.C.O. 10 generates a more coherent output frequency this frequency passes by way of the circuits 18 and 17 to the SAW device 12 where after being transmitted across the surface it passes through the amplifier 23 and reaches the phase comparator 11. The phase comparator now has two input signals at the output frequency of the V.C.O. 10 and one signal from the reference oscillator 16. Since the V.C.O. signals are more exactly the same frequency the phase comparator 11 tends to produce an output signal dependent on the phase difference between the two V.C.O. output signals with the result that the control signal for the V.C.O. 10 causes this oscillator to lock on to its own frequency rather than that of the reference oscillator, this frequency being dependent upon the surface condition of the SAW device 12, as explained above.

As variations in the surface condition of the SAW device 12 occur, or other perturbations occur, there is a tendency for the phase locked loop formed by the circuits 10 to 13, 17, 18 and 23 to fall out of lock. However, this tendency is largely overcome by the action of the modulating oscillator 22 which in 100% modulating the output of the reference oscillator 16 produces bursts of the reference signal at the input to the SAW device 10. The effect is to generate d.c. variations at the output of the phase comparator 11 which cause the frequency of the V.C.O. 10 to sweep over a small range, thus enabling it to lock again when perturbations occur. The level of the output of the modulating oscillator 22 can be varied by means of a d.c. offset control (not shown), allowing the percentage modulation in the modulator 19 to be varied as required. Should the phase lock loop fall seriously out of lock for any reason then the reference oscillator 16 re-establishes lock in the same way as when the circuit is first switched on.

The d.c. amplifier of FIG. 2 is no longer required since the phase comparator produces a reasonably large output from strong input signals (the V.C.O., and the reference oscillator or the modulated V.C.O. output) and frequency sweeping near the stable frequency of the V.C.O. is provoked by the modulating oscillator. Thus problems caused by noise from the d.c. amplifier are avoided.

The acoustic wave launched on the SAW device travels past the receiving electrodes to the end of the piezoelectric crystal where it is reflected and picked up on its return journey by the receive electrodes. The phase comparator 11 may therefore tend to function at least partly on the received wave and as a result the output frequency of the V.C.O. 10 may increase in frequency rather than decrease when the surface of the SAW 12 is more heavily loaded. Since about two thirds of the forward wave is absorbed by the receiving electrodes, this problem is not as serious as might be expected. The modulating oscillator 22 also reduces the effect of the reflected wave although its action in this respect is not fully understood and may depend on the position of the electrodes 3 and 4 in relation to the reflecting edge of the SAW device 10 and the repetition frequency of the oscillator 22. For this purpose the said repetition frequency may be selected for minimum reflection.

The signal applied to the transmit electrodes causes radio frequency radiation which is picked up by the receiving electrodes and possibly other parts of the circuit at the output side of the SAW device 12. The modulation introduced by the oscillator 22 causes a phase error between the high frequency pulses from the receive electrodes and by way of the r.f. radiation path reducing the noise effect produced by the r.f. signal.

It has been found that the circuit of FIG. 3 also operates (though not so well) if the output from the splitter 18 to the network 17 is connected instead to the input of the modulator 16 and the output of the reference oscillator is connected instead to the summing network 17.

Figure 4:
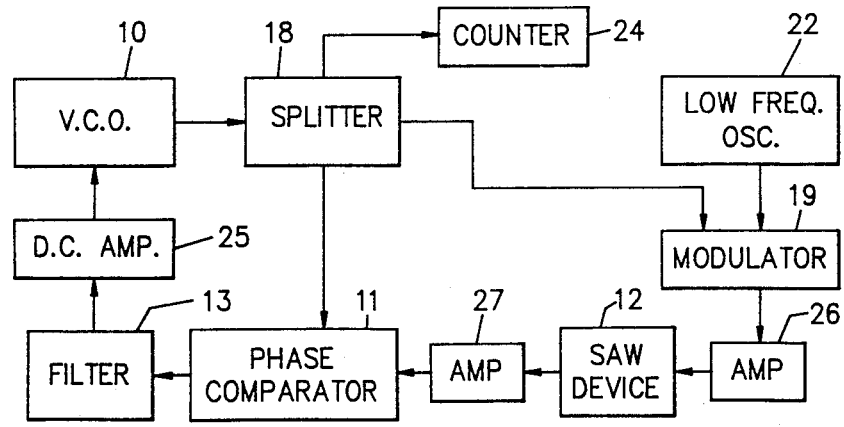
FIG. 4 is a block diagram of a circuit according to the invention using a modulating oscillator.

An alternative embodiment of the invention is shown in FIG. 4 where the reference oscillator 16, the summing network 17 and the amplifier 20 are omitted, and a d.c. amplifier 25 (between the filter 13 and the V.C.O. 10) and a.c. amplifiers 26 and 27 are added. The operation of this circuit is similar to that of FIG. 3 except that when the circuit is switched on or lock is lost there is no oscillator 16 to help establish lock. As a result the dynamic range of the circuit of FIG. 4 is not as great as that of FIG. 3 and it occasionally loses lock. Operation on switch-on and when lock is lost depends on the V.C.O. 10 establishing a reasonably coherent output at the stable frequency dictated by the current SAW condition to allow a control signal from the phase comparator 12 to be developed.

The arrangement of FIG. 4 may be modified by inserting a 90° delay between the splitter 18 and the modulator 19 (for example as part of the splitter 18). The delay in the SAW 12 is not very large and the extra delay provides a larger difference for the phase comparator 11. As a result the d.c. amplifier may, if required, be omitted.

The control signal to the V.C.O. 10 provides an alternative indication of the mass of analyte bound to the SAW, but it is probably not so accurate as the frequency of the V.C.O.

As mentioned above, the methods of using the invention usually rely on measuring the change of frequency of the voltage controlled oscillator before an analyte is bound to the crystal surface and afterwards. This change can be measured, for example, in two ways: with a liquid sample on the crystal surface so that the change in oscillator frequency occurs progressively; and by measuring the frequency when the crystal is coated with a reagent but no sample is present, applying the sample to the reagent so that the analyte becomes bound to the surface, washing and drying the crystal which then has the analyte and the reagent still on the surface, and finally measuring the oscillation frequency again. The second method is usually more satisfactory because the progressive change in frequency which occurs when the liquid sample is on the crystal tends to be somewhat erratic over the interval in which measurement is carried out. However the first method can be used if, for example, a computer is used to average oscillation frequencies.

For medical diagnostics, a number of crystals are prepared with electrodes deposited on them in a position such that when a crystal is inserted in a holder in apparatus having the circuit of FIG. 3 the electrodes are automatically connected into the circuit. The crystals are divided into groups with the surfaces of the crystals in each group at least partially coated with a reagent specific to that group. The reagents and therefore the groups are for different diagnostic purposes and in practice an operator selects a crystal with an appropriate coating for the test to be carried out and inserts it into the holder. At this stage the frequency of the V.C.O. 10 is noted from the counter 24. The crystal is withdrawn from the holer and a drop, of specified size, of a liquid sample is placed on the coated surface and left for a short period of time, for example about 10 minutes. Next the crystal is washed and dried and then it is replaced in the holder and a further measurement of the output frequency of the voltage controlled oscillator is carried out. The difference between the two frequency measurements provides an indication of the amount of analyte which has become bound to the crystal surface.

Since the type of reagents which can be used for this purpose and the way in which coating can be carried out and how the crystal can be handled in general are well known and do not form part of the present invention, they are not described here. The preparation of glass for medical diagnostics is discussed in "Immobilized Enzymes, Antigens, Antibodies and Peptides", edited by H. H. Weetall, published by Dekker, New York 1975 at page 191. Similar techniques can be used for piezoelectric crystals and ceramics.

It will be clear that the invention can be put into practice in many other ways than those specifically described so long as an oscillator is used which has an output frequency dependent on a control signal applied to the oscillator, and the control signal is derived from the delay between transmission and reception of a signal propagating acoustically on an SAW device. Stable oscillator frequencies of 30 MHz have been achieved and frequencies up to 100 to 300 MHz should be attainable without too much difficulty, allowing for the usual problems of high frequency operation, and will allow greatly increased sensitivity.

We claim:

1. Apparatus for obtaining an indication of an amount of an analyte bound to a piezoelectric device, comprising an electrical oscillator having a control terminal, the frequency of an output signal of the said oscillator being variable over a range in dependence upon the value of a control signal applied to the said control terminal, a piezoelectric device carrying a reagent for selectively binding an analyte to a surface of the device, launching and reception means coupled to the said device and to the said oscillator for use in launching acoustic waves at the output frequency of the said oscillator across the said device and for use in receiving acoustic waves propagating across the said device, and measurement means, with input coupled to the said launching and reception means and output coupled to the said control terminal, for deriving a signal representative of the time required for an acoustic wave to travel across the said device between launch and reception by the said launch and reception means, whereby the output frequency of the said oscillator depends on the speed of propagation of acoustic waves across the said device and therefore on the amount of analyte bound to said surface.

2. Apparatus according to claim 1 wherein the launching and reception means comprises means for making contact with first and second electrode means mounted on the said device in contact with the surface thereof, the first electrode means being for launching surface acoustic waves across the surface of the said device, and second electrode means for receiving the said acoustic waves and deriving an electrical signal representative thereof.

3. Apparatus according to claim 2 wherein the measurement means comprises
   phase-comparator means, having first and second inputs and an output, for generating an output signal having a value representative of any phase difference in signals applied to the first and second inputs, the first said input being coupled to the output of the said oscillator, the second input being coupled to the said second electrode means, and the said output being coupled to the said control terminal of the said oscillator.

4. Apparatus according to claim 3 wherein the said oscillator is a voltage-controlled oscillator, and the apparatus includes
   a low-frequency square-wave electrical oscillator having a repetition frequency at least an order of magnitude below the lowest frequency of the said voltage-controlled oscillator when the apparatus is in operation, and
   a modulator, having first and second inputs and an output, for generating an amplitude modulated signal at the said modulator output from signals applied at the first and second said modulator input terminals,
   the said voltage-controlled oscillator being coupled to the said means for making contact with the said first electrode means through the said modulator by way of the first said input and the said output of the said modulator, and
   the said second modulator input being coupled to the said low-frequency oscillator.

5. Apparatus according to claim 4 including means for introducing a 90° phase shift between the output of the said voltage-controlled oscillator and the first said input of the said modulator.

6. Apparatus according to claim 3 wherein the said oscillator is a voltage-controlled oscillator, and the apparatus includes
   a low-frequency rectangular-wave electrical oscillator having a repetition frequency at least an order of magnitude below the lowest frequency of the said voltage-controlled oscillator when the apparatus is in operation,
   a reference oscillator having an output frequency within the said range of the voltage-controlled oscillator,
   a modulator, having first and second inputs and an output, for generating an amplitude modulated signal at the said modulator output from signals applied at the first and second said modulator input terminals from the said low-frequency oscillator and the said reference oscillator, respectively,
   summing means having first and second inputs and an output providing an output signal which is representative of the sum (taking account of sign) of the instantaneous magnitudes of signals applied at the said first and second summing means inputs,
   the said voltage-controlled oscillator being coupled to the said means for making contact with the said first electrode means through the said summing means by way of the first said summing means input and the said output of the said summing means, and
   the said modulator being connected to the said second summing means input.

7. Apparatus according to claim 1 wherein the said launching and reception means comprise
   first and second interdigitated electrodes for launching acoustic waves on the surface of the device,
   third and fourth interdigitated electrodes for receiving said acoustic waves,
   a first connection used in coupling said first electrode to the said oscillator, the second electrode having no low conductivity connection to the said oscillator,
   a second connection used in coupling the said third electrode to the said measurement means, and
   a third connection used in coupling the said fourth electrode to a ground connection between the said oscillator and the said measurement means.

8. Apparatus for indicating the amount of material bound to the surface of a piezoelectric device, comprising
   a piezoelectric device carrying a reagent for selectively binding an analyte to a surface of the device, the device having first and second electrocde means mounted on the surface thereof for launching and receiving, respectively, acoustic waves on the said surface,
   first and second contact means for making electrical contact with the first and second electrode means, respectively,
   a voltage-controlled oscillator having a control terminal, the frequency of the said oscillator being variable over a range in dependence on the magnitude of a d.c. control signal applied to the said control terminal,
   phase-comparator means, having first and second inputs and an output, for generating a d.c. output signal of magnitude representaive of any phase difference in signals applied to the said first and second phase-comparator inputs, the first input being coupled to the said oscillator and the second input being coupled to the second contact means, and the said phase comparator output being coupled to the said control terminal.

9. Apparatus according to claim 8 including
   first and second electrode means mounted on the piezoelectric device for launching and receiving, respectively, acoustic waves on the said surface.

10. Apparatus according to claim 9 including
    a low-frequency electrical oscillator having an output frequency at least an order of magnitude below the lowest frequency of the said voltage controlled oscillator when the apparatus is in operation, and
    a modulator, having first and second inputs and an output, for generating an amplitude modulated signal at the said modulator output from signals applied at the first and second said modulator input terminals,
    the said voltage-controlled oscillator being coupled to the said first electrode means through the said modulator by way of the first said input and the said output of the said modulator, and
    the said second modulator input being coupled to the said low-frequency oscillator.

11. Apparatus according to claim 9 including
    a low-frequency rectangular-wave electrical oscillator having a repetition frequency at least an order of magnitude below the lowest frequency of the said voltage controlled oscillator when the apparatus is in operation, a reference oscillator having an output frequency within the said range of the voltage-controlled oscillator, a modulator, having first and second inputs and an output, for generating an amplitude modulated signal at the said modulator output from signals applied at the first and second said modulator input terminals from said low-frequency oscillator and the said reference oscillator, respectively, summing means having first and second inputs and an output providing an output signal which is representative of the sum (taking account of sign) of the instantaneous magnitudes of signals applied at the said first and second summing means inputs, the said voltage-controlled oscillator being coupled to the said first electrode means through the said summing means by way of the firsat said input summing means and the said output of the said summing means, and the said modulator being connected to the said second summing means input.

12. A method of obtaining an indication of the amount of analyte bound to a piezoelectric device, comprising the steps of applying a reagent to the device which selectively binds an analyte to said surface, obtaining an output signal from an electrical oscillator having a frequency which is variable over a range in dependence upon the value of a control signal applied to the said oscillator, using the said oscillator output signal to generate a launch signal to launch an acoustic wave across the device, receiving the said acoustic wave, deriving, from the said oscillator output and the received acoustic wave, a delay signal representative of the time required by an acoustic wave to travel across the said device between launch and reception, and deriving the said control signal for the said oscillator from the said delay signal, whereby the frequency of the said oscillator provides an indication of the said speed of propagation and therefore the amount of analyte bound to said surface.

13. A method as in claim 12 wherein the acoustic wave launched across the device is a surface wave.

14. A method according to claim 13 wherein deriving the said delay signal includes deriving an electrical signal from the said received acoustic wave, and deriving the said delay signal as representative of the relative phase of the said launch signal and the said electrical signal derived from the said received acoustic wave.

15. A method according to claim 14 including using a rectangular-wave modulating signal, having a repetition frequency at least an order of magnitude below the frequency of the said oscillator output signal, to modulate the said oscillator output signal in deriving the said launch signal.

16. A method according to claim 15, including summing the modulated oscillator output signal with the output signal of a reference oscillator having a frequency with the said range in deriving the said launch signal.

17. A method according to claim 12 of obtaining an indication of changes in amount of material bound to the said device including observing changes in the frequency of oscillation of the said oscillator over an interval in which the said change in amount may occur.

18. A piezoelectric device carrying a reagent for selectively binding an analyte to the surface of the said device, the said device having first and second electrodes in close proximity for launching acoustic waves on the surface of the crystal, third and fourth electrodes in close proximity but spaced from the said first and second electrodes for receiving acoustic waves on the said surface, a first connection for use in coupling said first electrode to an oscillator, the second electrode having no low conductivity connection for coupling the said second electrode to the said oscillator, a second connection for use in coupling the said third electrode to phase comparison means, and a third connection for coupling the said fourth electrode to a ground connection between the said oscillator and the said measurement means.

19. A method according to claim 18 including using a rectangular-wave modulating signal, having a repetition frequency at least an order of magnitude below the frequency of the said oscillator output signal, to modulate a reference signal having a frequency within the said range, and summing the modulated reference signal with the said oscillator output signal in deriving the said launch signal.

* * * * *